United States Patent
Cramer et al.

(10) Patent No.: US 9,182,370 B2
(45) Date of Patent: Nov. 10, 2015

(54) DEVICE FOR OPERATING A GAS SENSOR

(75) Inventors: Berndt Cramer, Leonberg (DE); Andy Tiefenbach, Farmington Hills, MI (US); Bernd Schumann, Rutesheim (DE); Thorsten Ochs, Schwieberdingen (DE); Helge Schichlein, Karlsruhe (DE)

(73) Assignee: ROBERT BOSCH GMBH, Stuttgart (DE)

( * ) Notice: Subject to any disclaimer, the term of this patent is extended or adjusted under 35 U.S.C. 154(b) by 2493 days.

(21) Appl. No.: 10/552,618

(22) PCT Filed: Apr. 6, 2004

(86) PCT No.: PCT/EP2004/050455
§ 371 (c)(1),
(2), (4) Date: Aug. 25, 2006

(87) PCT Pub. No.: WO2004/090524
PCT Pub. Date: Oct. 21, 2004

(65) Prior Publication Data
US 2007/0108053 A1    May 17, 2007

(30) Foreign Application Priority Data
Apr. 11, 2003  (DE) .................... 103 16 645

(51) Int. Cl.
*G01N 27/406* (2006.01)
*G01N 27/419* (2006.01)

(52) U.S. Cl.
CPC .................... *G01N 27/419* (2013.01)

(58) Field of Classification Search
CPC ........................ G01N 27/406–27/41

USPC ............... 204/421–429; 73/23.31–23.32; 205/783.5–785, 781
See application file for complete search history.

(56) References Cited

U.S. PATENT DOCUMENTS

| | | | | |
|---|---|---|---|---|
| 4,824,549 A * | 4/1989 | Hamada et al. | ............... | 204/410 |
| 4,927,517 A * | 5/1990 | Mizutani et al. | ............... | 204/406 |
| 5,312,538 A * | 5/1994 | Metrich | ........................ | 204/425 |
| 5,632,883 A | 5/1997 | Hoetzel | | |
| 5,895,564 A * | 4/1999 | Miyata et al. | .............. | 205/784.5 |
| 6,623,618 B1 * | 9/2003 | Kato et al. | .................... | 205/781 |
| 2002/0157452 A1 | 10/2002 | Cramer et al. | | |

FOREIGN PATENT DOCUMENTS

| | | |
|---|---|---|
| DE | 36 25 071 | 10/1987 |
| EP | 0 427 958 | 5/1991 |
| WO | WO 02/079769 | 10/2002 |

OTHER PUBLICATIONS

"Otto-Motor—Management/Bosch," Vieweg Publishing House, 1st edition, 1998, pp. 22-23.

* cited by examiner

*Primary Examiner* — Bach Dinh
(74) *Attorney, Agent, or Firm* — Kenyon & Kenyon LLP

(57) ABSTRACT

A device for operating a gas sensor having both at least one pump cell and a measuring cell is provided. A constant current source is provided that makes available a pump current which acts upon an outer electrode of the pump cell. The constant current source provides at least two different amounts of the pump current and/or allows for an alternating operation having ON phases and OFF phases, the duration of the ON phases/OFF phases being specifiable. The device may be largely implemented in digital circuitry and adapted to different requirements.

24 Claims, 3 Drawing Sheets

DEVICE FOR OPERATING A GAS SENSOR

FIELD OF THE INVENTION

The present invention relates to a device for operating a gas sensor.

BACKGROUND INFORMATION

In the reference book "*Otto-Motor—Management/Bosch*", Vieweg Publishing House, 1st edition, 1998, pages 22-23, a broadband lambda sensor is described, having a sensor chamber which is connected to a gas compartment via a diffusion barrier. Situated in the sensor chamber is an inner pump electrode which, together with an outer pump electrode and an electrolyte that is situated between the pump electrodes and conducts oxygen ions, forms a pump cell. Using the pump cell, oxygen ions of the gas can be pumped through the electrolyte out of, or into, the sensor chamber.

In addition to the pump cell, a measuring cell is provided that is disposed between the inner pump electrode and a reference-gas electrode, an electrolyte conducting oxygen ions likewise being situated between the inner pump electrode and the reference-gas electrode. The measuring cell corresponds to a Nernst cell, in which the potential difference forming in the thermodynamic equilibrium between the inner pump electrode and the air reference electrode is proportional to the logarithm of the relationship of the partial pressure of the gas to be analyzed in the sensor chamber and the partial pressure of the gas to be analyzed in the air reference.

A circuit configuration realized in analog circuitry has the task of influencing the oxygen partial pressure in the sensor chamber in such a way that the Nernst potential remains constant at a predefined value. For this purpose, the circuit configuration alters an electrical pump current which acts upon the outer pump electrode. The polarity and the amount of the pump current depend upon whether and by what amount the predefined Nernst potential is exceeded or not attained. The pump current obtained appears at a load resistor as voltage, which is a measure for the concentration of the gas to be analyzed.

The Published German Patent Application DE 36 25 071 describes a method for operating a sensor having variable ionic conductivity, as well as a device for implementing the method, in which the sensor, in cyclically proceeding operations, is acted upon in pulse-like fashion by a current supplied from a constant current source. The resulting voltage at the sensor is a measure for the relative atmospheric humidity to which the sensor is exposed. The pulse-like feeding of the current prevents polarization effects at the electrodes of the sensor. The use of a constant current, which can have an alternating polarity, permits a simple evaluation of the sensor voltage resulting at the sensor element.

An object of the present invention is to provide a device for operating a gas sensor, which contains a circuit configuration that is easy to implement and permits a precise, low-drift and low-offset measurement

SUMMARY

According to the present invention, a constant current source is provided for supplying the pump current. According to a first example embodiment, the constant current source is adjustable to several specifiable current levels.

According to a second example embodiment which, if desired, may be provided in addition to the first example embodiment, the constant current source allows for a clocked operation with ON phases and OFF phases, the duration of the ON phases and/or the duration of the OFF phases being specifiable.

The device of the present invention may be realized to a great extent in digital circuitry. A comparatively precise recording of the pump current, and therefore of the measuring signal, is thereby possible. The errors due to drift and offset, which in analog circuitry can only be controlled with costly measures, are avoided to the greatest extent possible. Moreover, the recording of the pump current is independent of an electrical capacitance of the gas sensor.

According to the first example embodiment, the device of the present invention allows the stipulation of different amounts of the constant currents. In a steady-state operating condition, in which the concentration of the gas to be measured does not change or changes only insignificantly within the measuring time interval considered, the constant current known in the circuit configuration is identical to the pump current. In the usually non-steady conditions, it is possible to obtain the pump current by a simple averaging over a temporally predefined measuring window. The averaging turns out to be particularly easy, since both the times in which the predefined constant current is flowing, and the amount of the constant current in the circuit configuration are known.

The second example embodiment, which allows for a clocked operation with ON phases and OFF phases, permits the stipulation of an average pump current by varying the duration of the ON phases and/or OFF phases. The second example embodiment permits a realization of the constant current source in the extreme case with only one specifiable level.

The most flexible design approach allows for a combination of the first and second example embodiments. The combination makes it possible to flexibly predefine the amounts of the constant currents and the duration of the ON phases and/or OFF phases. Since the device of the present invention for operating the gas sensor includes a control loop, which exists because a change in the pump current influences the measuring voltage that on its part can lead again to an adjustment of the pump current, using the measures provided according to the invention, it is possible to optimize the control response in view of accuracy and speed of the control.

The device according to the present invention may be directly addressed via standardized interfaces by further electrical control units which are not the subject matter of the present patent application. Only a small number of additional circuitry measures are necessary for this purpose. The signals occurring in the device of the present invention exist largely in digital form, so that the signal processing may take place to the greatest extent possible in a computer. This permits a miniaturization of the circuit configuration, while at the same time increasing the functionality and the possibility of altering the functionality of the device. Adaptation to different gas-sensor designs, or adaptation for the compensation of manufacturing tolerances of a gas-sensor series, is possible in a simple manner using software adaptations, without altering the hardware.

According to one example embodiment, the constant current source permits the stipulation of constant currents that have both positive and negative polarity.

One example embodiment allows for averaging over a predefined measuring time. The averaging makes it possible to increase accuracy in recording the pump current, particularly in the case of non-steady operations in which control actions occur. By adapting the measuring time, which corresponds to a low-pass filter function, the time characteristic of the pump current may be smoothed at the same time.

The device according to the present invention permits the ascertainment of the pump current by simple counting operations. Given a predefined current level and predefined duration of the ON phases and/or OFF phases, the count of the number of ON phases or OFF phases within the predefined measuring time represents a direct measure for the pump current. An automatic control of the measuring voltage is possible by a control of the constant current source as a function of a comparison between a predefined setpoint measuring voltage and the actual measuring voltage. The analog measuring voltage may be converted to a digital signal in an analog-to-digital converter, so that it is possible to implement the device of the present invention to the greatest extent possible in digital circuitry.

One further example embodiment of the device according to the present invention provides for a gas sensor which includes a plurality of pump cells that, for example, are able to be exposed to different gases to be analyzed. Only one measuring cell is needed for the plurality of pump cells. By a time coordination, one and the same constant current source is able to act upon all pump cells with one pump current in temporal sequence. If the resulting times yield values which are too high for the current-free state of some pump cells, the constant current source and its control may be provided multiple times accordingly. The additional expenditure is thereby limited, since the functions are able to be implemented repeatedly in a computer, e.g., a microprocessor, without great expenditure.

The device according to the present invention is particularly suitable for operating a gas sensor situated in the exhaust gas of an internal combustion engine. The far-reaching possibility of digitalization has important advantages in this use of the gas sensor with regard to the surroundings contaminated with electromagnetic disturbances.

DETAILED DESCRIPTION

Figure 1:
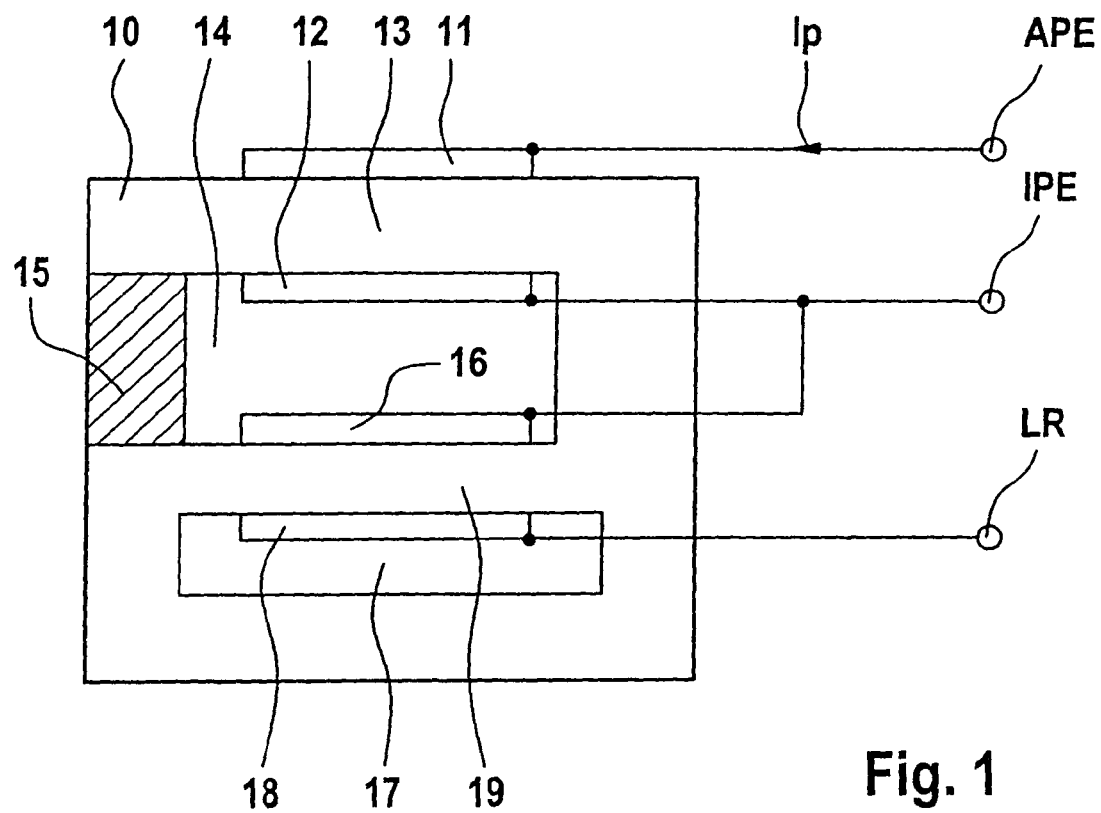
FIG. 1 shows a schematic cross-sectional view of a gas sensor.

FIG. 1 shows a schematic cross-sectional view of a gas sensor 10 which includes a pump cell 13 situated between an outer pump electrode 11 and an inner pump electrode 12. Inner pump electrode 12 is situated in a sensor chamber 14 that receives the gas to be measured via a diffusion barrier 15. Also situated in sensor chamber 14 is an inner measuring electrode 16 which, together with an outer measuring electrode 18 disposed in a gas reference space 17, forms a measuring cell 19.

Outer pump electrode 11, which is connected to a pump electrode connection APE, receives a pump current Ip. Inner pump electrode 12, which is electrically connected to inner measuring electrode 16, is connected to a sensor-chamber connection IPE. Outer measuring electrode 18 is connected to a measuring-signal connection LR.

Figure 2:
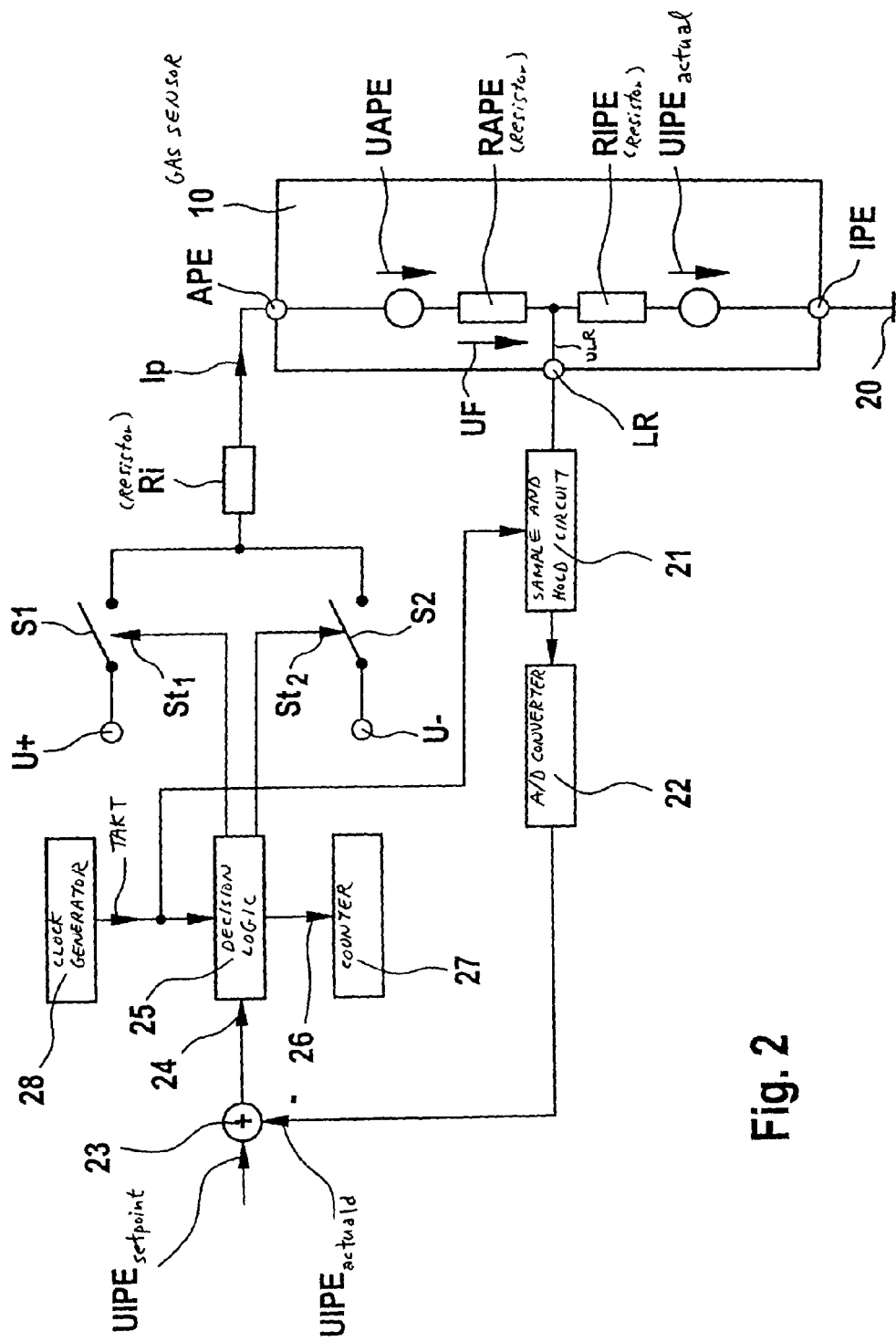
FIG. 2 shows a block diagram of an example embodiment of a device according to the present invention for operating the gas sensor shown in FIG. 1.

FIG. 2 shows a block diagram of a device for operating gas sensor 10. The equivalent electrical circuit diagram of gas sensor 10 has a pump-cell voltage UAPE and a pump-cell resistor RAPE between pump-electrode connection APE and measuring-signal connection LR. Gas sensor 10 further has a measuring voltage UIPEactual and a measuring-cell resistor RIPE between measuring-signal connection LR and sensor-chamber connection IPE. Sensor-chamber connection IPE is connected to a circuit ground 20.

Measuring-signal connection LR, to which a sensor voltage ULR is applied, is connected to a sample-and-hold circuit 21 that is connected in series to an analog-to-digital converter 22, which transmits a digitalized measuring voltage UIPEactuald to a comparator 23. Comparator 23 compares digitalized measuring voltage UIPEactuald to a setpoint voltage UIPEsetpoint and emits a differential signal 24 to a decision logic 25. Decision logic 25 emits a first switching signal St1 to a first switch S1, a second switching signal St2 to a second switch S2, and a counting signal 26 to a counter 27.

First switch S1 is connected to a positive voltage source U+, and the second switch is connected to a negative voltage source U−. First switch S1 is able to switch positive voltage source U+, and second switch S2 is able to switch negative voltage source U− to a current-source resistor Ri, that is connected to pump-electrode connection APE, into which pump current Ip flows. To control sample-and-hold circuit 21 and decision logic 25, a clock generator 28 is provided that supplies a clock signal TAKT.

Figure 3A:
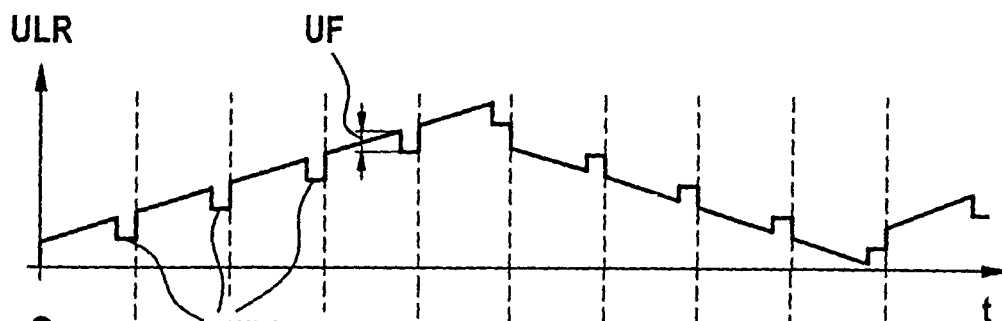
FIGS. 3a-3c show various signal patterns as a function of time, which occur in the configuration shown in FIG. 2.
Figure 3B:
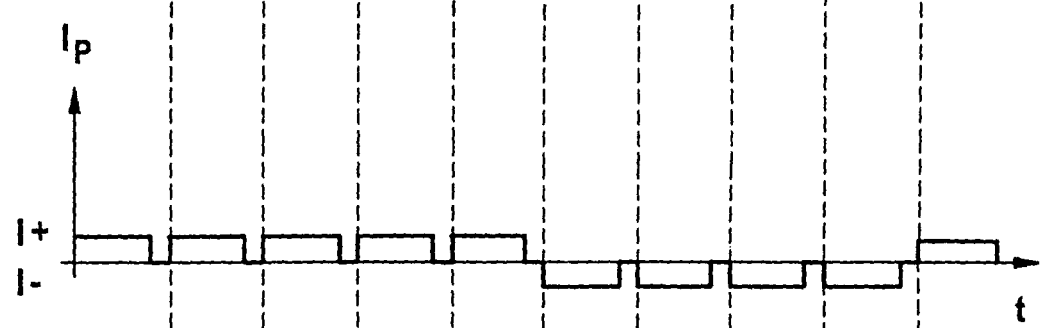
Figure 3C:
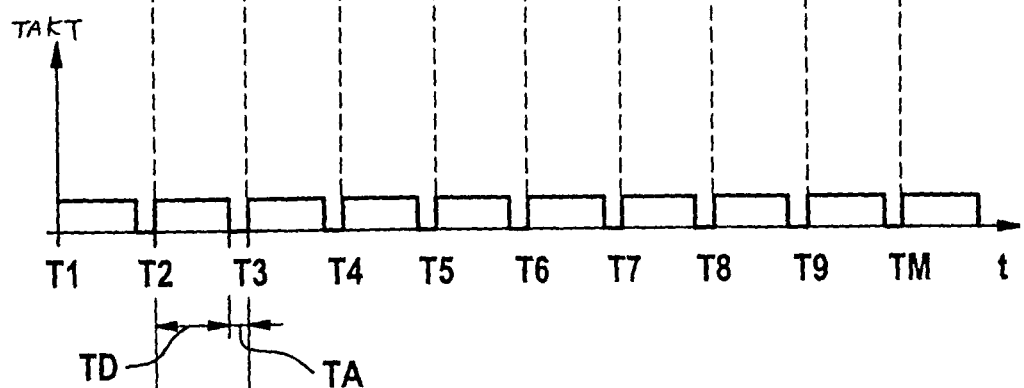

FIGS. 3a-3c show various signal patterns as a function of time t, which occur in the device shown in FIG. 2.

FIG. 3a shows sensor voltage ULR as a function of time t. Sensor voltage ULR is obtained from the superimposition of the voltage of measuring-voltage source UIPEactual and a fault voltage UF, which is obtained due to the voltage drop at pump-cell resistor RAPE based on pump current Ip. Fault voltage UF occurs during ON phases TD, i.e., while pump current Ip is flowing. During OFF phases TA, pump current Ip is interrupted, so that measuring voltage UIPEactual is present as sensor voltage ULR.

FIG. 3b shows pump current Ip as a function of time t. In a first time interval, which is between a first and a sixth instant Ti, T6, during ON phases TD, pump current Ip occurs with a first amount I+. During OFF phases TA and during a time interval which begins after sixth instant T6 and ends at a measuring time TM, pump current Ip during ON phases TD is established at a second amount I−. With the occurrence of measuring time TM, the amount of pump current Ip during ON phase TD changes again to first amount I+.

FIG. 3c shows clock signal TAKT as a function of time t. During ON phases TD, clock signal TAKT has an ON level, and during OFF phases TA, an OFF level. Clock signal TAKT has a period duration TP. ON phase TD and OFF phase TA occur within period duration TP.

The device according to the present invention for operating gas sensor 10 shown schematically in FIG. 1 is explained in greater detail in connection with the signal patterns, shown in FIGS. 3a-3c, which occur in the configuration shown in FIG. 2:

Gas sensor 10 is situated, for example, in the exhaust gas of an internal combustion engine. In this practical application, gas sensor 10 detects a concentration of a gaseous component contained in the exhaust gas. It may be the residual oxygen concentration, for instance, or the nitrogen oxide (NOx) concentration. Outer pump electrode 11 and diffusion barrier 15 are exposed to the gas to be analyzed. The gas concentration in sensor chamber 14 may be altered by a gaseous-ion transport using pump cell 13. The concentration may be changed by applying a voltage to pump-electrode connection APE of outer pump electrode 11. Pump current Ip results based on the voltage.

Gas sensor 10 also includes measuring cell 19 formed between inner and outer measuring electrodes 16, 18. The concentration of the gas to be analyzed in sensor chamber 14 may be measured by measuring cell 19 on the basis of a flow of gaseous ions occurring in measuring cell 19. The voltage of measuring cell 19 is measuring voltage UIPEactual, known as Nernst voltage. A prerequisite for the formation of the Nernst voltage is a thermodynamic equilibrium between the gaseous components of the gas to be analyzed. The concentration measurement is carried out as against the gas concentration which occurs in gas reference space 17. It is a space filled, for example, with air.

On condition that the concentration of the gas to be measured in gas reference space 17 is higher than the concentration in sensor chamber 14, the equivalent circuit diagram of gas sensor 10 shown in FIG. 2 is applicable. Under the assumption indicated, the potential appearing at measuring-signal connection LR lies below the potential appearing at pump-electrode connection APE, but above the potential appearing at sensor-chamber connection IPE. The potentials are determined by the voltage sources shown in the equivalent circuit diagram of gas sensor 10 shown in FIG. 2. The voltages of the voltage sources, therefore measuring voltage UIPEactual and the pump-cell voltage of UAPE, are determined by the differences in concentration at measuring cell 19 and pump cell 13, respectively, which can be influenced by pump current Ip.

The configuration shown in FIG. 2 has the task of adjusting measuring voltage UIPEactual to setpoint voltage UIPEsetpoint. In the case of a gas sensor 10 which is intended to detect the concentration of the residual oxygen in the exhaust gas of an internal combustion engine in thermodynamic equilibrium, setpoint voltage UIPEsetpoint is set to a value, for example, which lies in the range of the air ratio lambda of at least approximatively=1, at which the oxygen concentration or the oxygen partial pressure changes by several powers of ten. Measuring voltage UIPEactual changes sharply accordingly. Setpoint voltage UIPEsetpoint is set, e.g., to a value of 450 mV.

Sensor voltage ULR shown in FIG. 3a, which is tapped off at measuring-signal connection LR, is measured during OFF phases TA. The falsification of the voltage by fault voltage UF on the basis of pump current Ip at measuring-cell resistor RIPE is not applicable during OFF phases TA of pump current Ip. Sensor voltage ULR is sampled by sample-and-hold circuit 21, controlled by clock signal TAKT, which is connected in series to and in front of analog-to-digital converter 22. Alternatively, sample-and-hold circuit 21 and analog-to-digital converter 22 may be interchanged in the configuration, so that an analog-to-digital conversion of measuring voltage UIPEactual may be provided immediately.

Digitalized measuring voltage UIPEactuald is compared to setpoint voltage UIPEsetpoint in comparator 23. Differential signal 24 is output to decision logic 25 as a function of the difference. Decision logic 25 activates either first switch S1 or second switch S2 using first switching signal St1 or second switching signal St2. The closing of first switch S1, which is connected to positive voltage source U+, leads, in conjunction with current-source resistor Ri, to a pump current Ip having predefined magnitude I+, shown in FIG. 3b, which occurs within a time interval that lies between first instant T1 and sixth instant T6. First control signal St1, and therefore the occurrence of pump current Ip having first amount I+, occurs during ON phases TD. In the exemplary embodiment shown, five ON phases TD are provided between first and sixth instants T1, T6.

In the exemplary embodiment shown, the configuration having positive or negative voltage source U+, U− and current-source resistor Ri, is intended to form a switchable constant current source. Instead of the example embodiments shown, the constant current source may also be implemented with a greater degree of complexity, with the aim of being able to specify the pump current more precisely. On condition that current-source resistor Ri is of considerably higher resistance than the internal resistance of positive or negative voltage source U+, U− and greater than pump-cell resistor Ri, pump current Ip is determined essentially by the voltage of positive or negative voltage source U+, U− and current-source resistor Ri. If only one predefined amount of pump current Ip is provided, the constant current source may be set to current levels I+, I− shown in FIG. 3b. By changing the voltage of positive and negative voltage sources U+, U− and/or the resistance value of current-source resistor Ri, it is possible to predefine different current levels.

Upon closure of second switch S2, which is connected to negative voltage source U−, in conjunction with current-source resistor Ri, the second amount I− of pump current Ip results. This situation is shown between the sixth instant and measuring time TM in FIG. 3b. For example, the four ON durations TD shown occur within the time interval. In the exemplary embodiment shown, it is assumed that at sixth instant T6, differential signal 24 signals that digitalized measuring voltage UIPEactuald has exceeded setpoint voltage UIPEsetpoint, so that in period duration TP following instant T6, first switching signal St1 is withdrawn and second switching signal St2 is output during ON phases TD for closing second switch S2. With the occurrence of measuring time TM, differential signal 24 changes again. With the occurrence of measuring time TM, one control oscillation is ended. A different embodiment of the automatic controller may lead to a different behavior.

Because of the largely digital implementation of circuit components, pump current Ip may be easily ascertained. First and second amounts I+, I− of the current of the constant current source are established by the voltage of positive and negative voltage sources U+, U−, and by the amount of current-source resistance Ri. Pump current Ip may be ascertained by a simple counting operation of ON phases TD shown in FIG. 3b, provided first and second amounts I+, I− of pump current Ip are of equal value. The counting is accomplished by a count of ON durations TD occurring between first and sixth instants T1, T6, and a count of ON durations TD occurring between sixth instant T6 and measuring time TM. The difference is subsequently formed.

In the exemplary embodiment shown, measuring time TM, over which the sum operation is carried out, is coincidentally exactly equated to one control oscillation. Measuring time TM may be specified independently of the control oscillation. Measuring time TM indicates the integration time for the averaging. The result of the averaging yields average pump current Ip acting upon outer pump electrode 11. Pump current Ip is a direct measure for the concentration of the gas to be analyzed, since the automatic control of pump current Ip is regulated as a function of constantly retained measuring voltage UIPEactual. The averaging may be carried out in sliding fashion. Sliding averaging means that, for example, the current pulses are summed at each instant T1-T9, up to the uniformly progressing measuring time TM.

The resolution in ascertaining average pump current Ip is influenced by the determination of measuring time TM. For example, if period duration TP is set to 0.1 ms and measuring time TM is set to 10 ms, then the resolution amounts to TM/TP=100. Average pump current Ip may therefore be resolved in 1/100 steps of maximum possible average pump current Ip. In this context, the maximum possible average value of pump current Ip may amount to 100*U+*TD/Ri or 100*U−*TD/Ri.

By stepping (or graduation) of ON durations TD and/or of first and/or second amount I+, I−, it is possible to optimize the control response with regard to accuracy and speed, and especially stability of the control.

A further example embodiment may provide that constant current source U+, S1, U−, S2, Ri is designed to be multi-step, in particular multi-step for both polarities, as well. If differential signal 24 indicates a larger difference between measuring voltage UIPEactual and setpoint voltage UIPEsetpoint, a higher current amount may be specified for one or more ON times TD than in the case of a smaller difference.

In another example embodiment, ON phases TD and/or period duration TP are variably specified. In this case, in response to a higher difference between measuring voltage UIPEactual and setpoint voltage UIPEsetpoint, initially a longer ON phase TD may be specified for one or more period durations TP than if the difference were smaller.

One example embodiment provides for a combination of the further developments, so that with a change in the amounts I+, I− of pump current Ip, as well as a change in ON phases TD and/or period durations TP, the quantity of electricity supplied to pump electrode 11 may be variably predefined according to the product Ip*TD in one period duration TP.

In the case of the further example embodiment, the change in pump current Ip to the other amounts I+, I−, as well as the change in the duration of ON phases TD are to be taken into consideration in the counting of ON phases TD in counter 27.

In another further example embodiment, instead of the one pump cell 13, gas sensor 10 has further pump cells. The individual pump cells may receive pump current Ip from constant current source U+, S1, U−, S2, Ri in temporal sequence. However, a plurality of constant current sources may also be provided corresponding to the number of pump cell 13. To avoid a voltage drop in gas sensor 10 while sample-and-hold circuit 21 is sampling measuring voltage UIPEactual, care must be taken that OFF phases TA exist simultaneously for all pump cells.

What is claimed is:

1. A gas sensor device, comprising:
    a sensor chamber that receives via a diffusion barrier a gas to be analyzed;
    at least one pump cell situated between the sensor chamber and the gas to be analyzed, wherein the at least one pump cell is exposed to the gas to be analyzed and includes an outer pump electrode;
    a measuring electrode situated in a reference-gas space;
    a measuring cell situated between the sensor chamber and the reference-gas space, wherein the outer pump electrode of the pump cell exposed to the gas to be analyzed receives a pump current which depends on a measuring voltage that is applied to the measuring electrode situated in the reference-gas space; and
    a constant current source for supplying the pump current, wherein the constant current source is configured to be set to at least two values of the pump current, and wherein for alternating operation, including ON phases and OFF phases, the duration of the ON phases and OFF phases is a specified constant.

2. The device as recited in claim 1, wherein the constant current source specifies a positive polarity value and a negative polarity value for the pump current.

3. The device as recited in claim 2, wherein the device is configured to determine an average of the pump current over a predefined measuring time.

4. The device as recited in claim 3, wherein the device is configured to determine the average pump current by varying the duration of at least one of the ON phases and OFF phases.

5. The device as recited in claim 3, wherein the constant current source specifies a positive polarity value and a negative polarity value for the pump current, wherein the device is configured to determine an average of the pump current over a predefined measuring time, and wherein the measuring voltage is recorded during the OFF phases.

6. The device as recited in claim 5, wherein the constant current source is controlled as a function of a differential signal of a comparator resulting from the difference between the measuring voltage and a setpoint voltage, wherein a plurality of pump cells is provided, and the outer electrode of each pump cell receives the pump current, wherein air is present in the reference-gas space, wherein the setpoint voltage is set to a value between 300 mV to 700 mV, and wherein the gas sensor device is an exhaust-gas sensor, and wherein the outer pump electrode and the diffusion barrier are exposed to the exhaust gas.

7. The device as recited in claim 3, wherein the device is configured to determine the average pump current by varying the duration of at least one of the ON phases and OFF phases.

8. The device as recited in claim 2, wherein the measuring voltage is recorded during the OFF phases.

9. The device as recited in claim 2, wherein the constant current source is controlled as a function of a differential signal of a comparator resulting from the difference between the measuring voltage and a setpoint voltage.

10. The device as recited in claim 9, wherein air is present in the reference-gas space.

11. The device as recited in claim 10, wherein the setpoint voltage is set to a value between 300 mV to 700 mV.

12. The device as recited in claim 2, wherein a plurality of pump cells is provided, and the outer electrode of each pump cell receives the pump current.

13. The device as recited in claim 2, wherein the constant current source is controlled as a function of a differential signal of a comparator resulting from the difference between the measuring voltage and a setpoint voltage, wherein a plurality of pump cells is provided, and the outer electrode of each pump cell receives the pump current, wherein air is present in the reference-gas space, wherein the setpoint voltage is set to a value between 300 mV to 700 mV, and wherein the gas sensor device is an exhaust-gas sensor, and wherein the outer pump electrode and the diffusion barrier are exposed to the exhaust gas.

14. The device as recited in claim 2, further comprising:
    a sample-and-hold circuit, which is connected to the measuring electrode situated in the reference-gas space;
    an analog-to-digital converter, which is in series with the sample-and-hold circuit; and
    a comparator which receives a digitized voltage from the analog-to-digital converter.

15. The device as recited in claim 1, wherein the gas sensor device is an exhaust-gas sensor, and wherein the outer pump electrode and the diffusion barrier are exposed to the exhaust gas.

16. A device for operating a gas sensor, comprising:
    a constant current source for supplying a pump current, wherein the constant current source is configured to be set to at least two values of the pump current, and wherein for alternating operation, including ON phases and OFF phases, the duration of the ON phases and OFF phases is a specified constant, and wherein the gas sensor includes:
    a sensor chamber that receives via a diffusion barrier a gas to be analyzed;
    at least one pump cell situated between the sensor chamber and the gas to be analyzed,
    wherein the at least one pump cell is exposed to the gas to be analyzed and includes an outer pump electrode;
    a measuring electrode situated in the reference-gas space; and
    a measuring cell situated between the sensor chamber and the reference-gas space;

wherein the outer pump electrode of the pump cell exposed to the gas to be analyzed receives the pump current which depends on a measuring voltage that is applied to the measuring electrode situated in the reference-gas space.

17. The device as recited in claim 16, wherein the constant current source specifies a positive polarity value and a negative polarity value for the pump current.

18. The device as recited in claim 17, wherein the device is configured to determine an average of the pump current over a predefined measuring time.

19. The device as recited in claim 18, wherein the device is configured to determine the average pump current by varying the duration of at least one of the ON phases and OFF phases.

20. The device as recited in claim 17, wherein the measuring voltage is recorded during the OFF phases.

21. The device as recited in claim 17, wherein the constant current source is controlled as a function of a differential signal of a comparator resulting from the difference between the measuring voltage and a setpoint voltage.

22. The device as recited in claim 21, wherein the setpoint voltage is set to a value between 300 mV to 700 mV.

23. The device as recited in claim 17, wherein a plurality of pump cells is provided, and the outer electrode of each pump cell receives the pump current.

24. The device as recited in claim 16, further comprising:
    a sample-and-hold circuit, which is connected to a measuring electrode situated in the reference-gas space;
    an analog-to-digital converter, which is in series with the sample-and-hold circuit; and
    a comparator which receives a digitized voltage from the analog-to-digital converter.

* * * * *